United States Patent
Ma et al.

(10) Patent No.: US 12,226,772 B2
(45) Date of Patent: Feb. 18, 2025

(54) BIOCHIP AND MANUFACTURING METHOD THEREOF

(71) Applicant: BOE TECHNOLOGY GROUP CO., LTD., Beijing (CN)

(72) Inventors: Xiaochen Ma, Beijing (CN); Ce Ning, Beijing (CN); Guangcai Yuan, Beijing (CN); Xin Gu, Beijing (CN); Zhengliang Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 725 days.

(21) Appl. No.: 17/432,580

(22) PCT Filed: Jan. 22, 2021

(86) PCT No.: PCT/CN2021/073249
§ 371 (c)(1),
(2) Date: Aug. 20, 2021

(87) PCT Pub. No.: WO2021/147988
PCT Pub. Date: Jul. 29, 2021

(65) Prior Publication Data
US 2022/0126294 A1    Apr. 28, 2022

(30) Foreign Application Priority Data

Jan. 22, 2020 (CN) .......................... 202010075614.1

(51) Int. Cl.
*B01L 3/00* (2006.01)
*C23C 14/04* (2006.01)
*C23C 14/34* (2006.01)

(52) U.S. Cl.
CPC ........ *B01L 3/502753* (2013.01); *C23C 14/04* (2013.01); *C23C 14/34* (2013.01);
(Continued)

(58) Field of Classification Search
CPC ......... B01L 2200/025; B01L 2200/027; B01L 2200/0631; B01L 2200/0652;
(Continued)

(56) References Cited

U.S. PATENT DOCUMENTS

2008/0280785 A1* 11/2008 Tseng .................... B01L 3/0255
506/40
2010/0003421 A1   1/2010 Ebels et al.
2013/0000764 A1   1/2013 Li et al.

FOREIGN PATENT DOCUMENTS

CN            1515898 A    7/2004
CN          201004062 Y    1/2008
(Continued)

OTHER PUBLICATIONS

China Patent Office, CN202010075614.1 First Office Action issued on Apr. 6, 2022.

*Primary Examiner* — Jennifer Wecker
*Assistant Examiner* — Jonathan Bortoli
(74) *Attorney, Agent, or Firm* — HOUTTEMAN LAW LLC

(57) ABSTRACT

A biochip and a method for manufacturing the same are provided. The biochip includes: a guide layer; a channel layer on the guide layer, wherein the channel layer has therein a plurality of first channels extending in a first direction; a plurality of second channels extending in a second direction, wherein each of the plurality of second channels is in communication with the plurality of first channels, the plurality of second channels are in a layer where the channel layer is located, or in a layer where the channel layer and the guide layer are located; an encapsulation cover plate on a side of the channel layer distal to the guide layer; and a driving unit configured to drive biomolecules to move.

19 Claims, 9 Drawing Sheets

(52) U.S. Cl.
CPC ... *B01L 2200/025* (2013.01); *B01L 2200/027* (2013.01); *B01L 2200/0631* (2013.01); *B01L 2200/0652* (2013.01); *B01L 2300/042* (2013.01); *B01L 2300/0819* (2013.01); *B01L 2300/0896* (2013.01); *B01L 2400/0421* (2013.01)

(58) Field of Classification Search
CPC .......... B01L 2200/10; B01L 2300/042; B01L 2300/0645; B01L 2300/0819; B01L 2300/0861; B01L 2300/0896; B01L 2300/12; B01L 2400/0421; B01L 3/502707; B01L 3/502753; B01L 2200/0621; B01L 2300/0864; B01L 2300/0887; C23C 14/04; C23C 14/34; C12M 1/00

See application file for complete search history.

(56) References Cited

FOREIGN PATENT DOCUMENTS

| | | | |
|---|---|---|---|
| CN | 101274469 A | 10/2008 | |
| CN | 101423188 A | 5/2009 | |
| CN | 102951591 A | 3/2013 | |
| CN | 103894248 A | 7/2014 | |
| CN | 104190483 A | 12/2014 | |
| CN | 104546669 A | 4/2015 | |
| CN | 207401491 U | 5/2018 | |
| CN | 109060922 A | 12/2018 | |
| JP | 2013130409 A | 7/2013 | |
| WO | WO 2006102516 A2 | 9/2006 | |
| WO | WO-2020092975 A2 * | 5/2020 | ........ B01L 3/502761 |

* cited by examiner

BIOCHIP AND MANUFACTURING METHOD THEREOF

CROSS-REFERENCE TO RELATED APPLICATIONS

This is a National Phase Application filed under 35 U.S.C. 371 as a national stage of PCT/CN2021/073249 filed on Jan. 22, 2021, an application claiming the priority of the Chinese Patent Application No. 202010075614.1 filed on Jan. 22, 2020, the content of each of which is incorporated herein by reference in its entirety.

TECHNICAL FIELD

The present disclosure relates to the field of biochip technology, in particular to a biochip and a manufacturing method thereof.

BACKGROUND

Biomolecules with different sizes or charge quantities (i.e., quantities of charges) have different movement tracks (or motion trajectories) under the action of cross electric fields or cross fluid forces. A biomolecule separation chip based on an Anisotropic Nanofilter Array (ANA) (hereinafter, referred to as "ANA biochip") is a biochip for simultaneously separating and purifying a plurality of different biomolecules according to differences in the movement tracks of the plurality of biomolecules.

In the prior art, the ANA biochip is generally manufactured by a silicon process. That is, on a base plate made of a silicon (Si) material, a silicon tip array manufacturing process (which may be an Electron Beam Lithography (EBL) process) and an exposure process are adopted to perform high-precision etching to form interleaved micro grooves and nano grooves in the silicon base plate; then, a cover plate is used as the tops of the nano grooves and the micro grooves; a high-precision bonding is performed on the silicon base plate and the cover plate, such that the cover plate is used as the tops of micron channels and nano channels to form sealed micron channels and sealed nano channels; and then, the micron channels and the nano channels may be adopted to separate biomolecules.

SUMMARY

A first aspect of the present disclosure provides a biochip, including:
a guide layer;
a channel layer on the guide layer, wherein the channel layer has therein a plurality of
first channels extending in a first direction;
a plurality of second channels extending in a second direction, wherein each of the plurality of second channels is in communication with the plurality of first channels, the plurality of second channels are in a layer where the channel layer is located, or in a layer where the channel layer and the guide layer are located;
an encapsulation cover plate on a side of the channel layer distal to the guide layer; and
a driving unit configured to drive biomolecules to move.

In an embodiment, a plurality of first grooves extending along the first direction are on a side of the guide layer proximal to the channel layer, and are in one-to-one correspondence with the plurality of first channels, and an orthographic projection of each of the plurality of first channels on the guide layer is within an orthographic projection of a corresponding one of the plurality of first grooves on the guide layer.

In an embodiment, the plurality of second channels includes a plurality of second grooves, and in a direction perpendicular to both the first direction and the second direction, a height of each of the plurality of second grooves is larger than a height of each of the plurality of first channels, and smaller than a sum of heights of a layer where the channel layer is located and a layer where the guide layer is located.

In an embodiment, the biochip further includes: a planarization layer between the channel layer and the encapsulation cover plate.

In an embodiment, the biochip further includes:
a first liquid storage structure in communication with first ends of one or more of the plurality of first channels and configured to store a mixed solution having unseparated biomolecules; and
a plurality of second liquid storage structures in one-to-one correspondence with and in communication with second ends of the plurality of first channels, respectively, and configured to store solutions having separated biomolecules, respectively.

In an embodiment, the plurality of first channels are arranged sequentially along the second direction, and the first liquid storage structure is in communication with a first end of a first one of the plurality of first channels arranged along the second direction.

In an embodiment, the driving unit includes a first separation electrode and a second separation electrode, wherein
an orthographic projection of the first separation electrode on the guide layer at least partially overlaps an orthographic projection of the first liquid storage structure on the guide layer, and an orthographic projection of the second separation electrode on the guide layer at least partially overlaps an orthographic projection of the plurality of second liquid storage structures on the guide layer.

In an embodiment, each of the plurality of second channels has a height on the order of hundreds of microns, and each of the plurality of first channels has a height less than 200 nm.

In an embodiment, the plurality of first channels are separated from each other along the second direction, and the plurality of second channels are separated from each other along the first direction.

In an embodiment, a dimension of each of the plurality of first channels in a direction perpendicular to the first direction is greater than a diameter of each of the biomolecules.

In an embodiment, a dimension of each of the plurality of second channels in a direction perpendicular to the second direction is greater than a diameter of each of the biomolecules.

In an embodiment, an angle between the first direction and the second direction is an acute angle.

In an embodiment, the first direction and the second direction are perpendicular to each other, the driving unit further includes a plurality of sets of driving electrodes in one-to-one correspondence with the plurality of second channels;
the first and second separation electrodes are arranged along the first direction; and
each set of the plurality of sets of driving electrodes includes two driving electrodes arranged along the second direction and respectively at both ends of the corresponding second channel.

A second aspect of the present disclosure provides a manufacturing method for a biochip, including:

forming a guide layer;

forming a channel layer on the guide layer, wherein the forming a channel layer on the guide layer includes: forming a plurality of first channels extending in a first direction in the channel layer;

forming a plurality of second channels extending along a second direction in a layer where the channel layer is located, or in a layer where the channel layer and the guide layer are located, such that each of the plurality of second channels is in communication with the plurality of first channels;

forming a encapsulation cover plate on a side of the channel layer distal to the guide layer; and forming a driving unit configured to drive biomolecules to move.

In an embodiment, the forming a channel layer on the guide layer includes:

forming a channel layer on the guide layer by a thin film deposition process.

In an embodiment, the forming a guide layer includes:

forming a material layer as the guide layer;

forming a plurality of first grooves extending along the first direction on a side of the guide layer proximal to the channel layer;

the forming a channel layer on the guide layer includes:

forming the plurality of first channels in one-to-one correspondence with the plurality of first grooves in the channel layer at positions corresponding to the plurality of first grooves, due to deposition rates of a material of the channel layer at each hump and each recess of the plurality of first grooves being different from each other during the forming a channel layer on the guide layer, through a thin film deposition process.

In an embodiment, the forming a plurality of first grooves extending along the first direction on a side of the guide layer proximal to the channel layer includes:

forming the plurality of first grooves extending along the first direction on the side of the guide layer proximal to the channel layer through any one or any combination of: an etching process, an electron beam lithography process, a nano-imprinting process, and a thermal etching process.

In an embodiment, the forming a plurality of second channels extending along a second direction in a layer where the channel layer is located, or in a layer where the channel layer and the guide layer are located, such that each of the plurality of second channels is in communication with the plurality of first channels includes:

forming the plurality of second grooves which extend in the second direction and are in communication with each of the plurality of first channels, on the layer where the channel layer is located, or on the layer where the channel layer and the guide layer are located, by using a mask corresponding to a pattern of each of the plurality of second channels, through an etching process, thereby forming the plurality of second channels.

In an embodiment, the manufacturing method further includes:

forming a planarization layer on the channel layer.

In an embodiment, the guide layer is made of a material of glass.

DETAIL DESCRIPTION OF EMBODIMENTS

Figure 1:
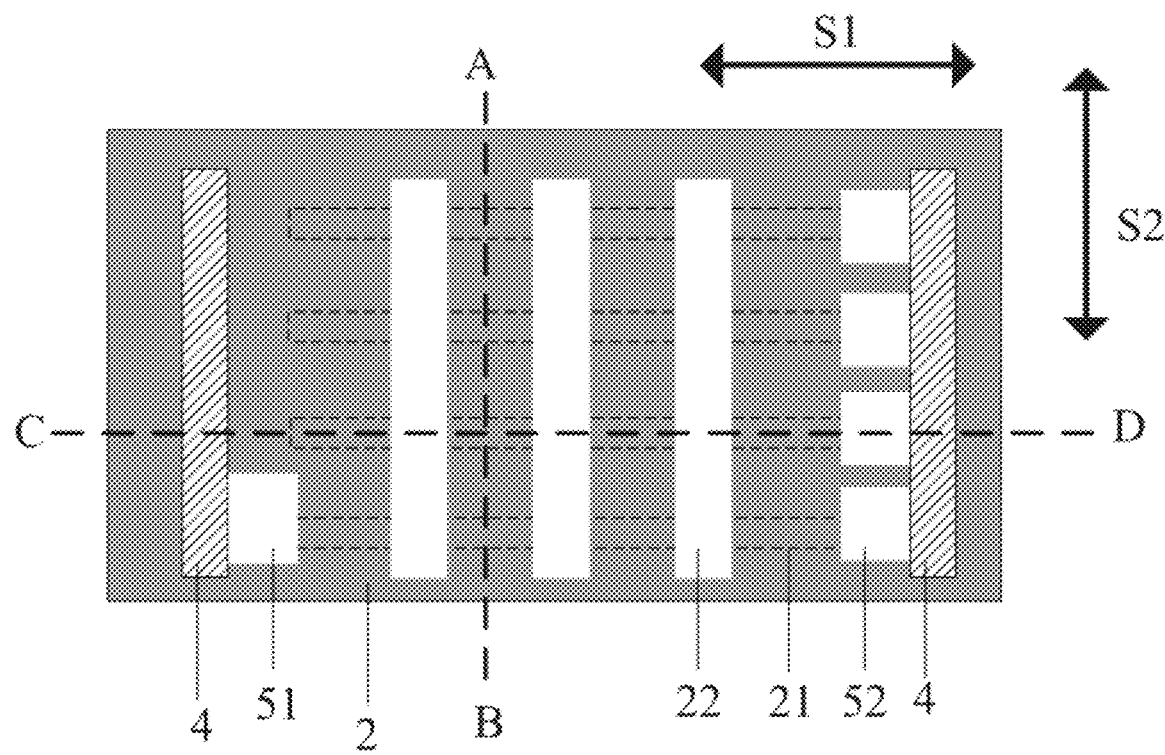
FIG. 1 is a schematic structural diagram (top view) of an implementation of a biochip according to an embodiment of the present disclosure.

To make the objects, technical solutions and advantages of the present disclosure more apparent, the present disclosure will be described in further detail with reference to the accompanying drawings. Obviously, the described embodiments are only some embodiments of the present disclosure, but not all embodiments. All other embodiments, which can be derived by a person skilled in the art from the embodiments of the present disclosure without any creative effort, shall fall within the protection scope of the present disclosure.

Shapes and sizes of components in the drawings are not necessarily to scale, emphasis instead being placed upon illustrating the embodiments of the present disclosure.

In the prior art, the ANA biochip manufactured by using the silicon process has many problems that are difficult to overcome. For example, the nano channels formed by attaching the cover plate and the silicon base plate to each other are limited by the attachment precision, which results in non-uniform structures of the nano channels. Further, it is difficult to manufacture a large-area ANA biochip due to the limitation of a size of a silicon wafer of a monocrystalline silicon. The etching process for the silicon base plate is required to have a high precision, and has a high difficulty; due to the limitation of the requirement of the etching precision of the silicon base plate, the manufacturing method for the ANA biochip manufactured by adopting the silicon process cannot be suitable for a glass base plate which may be produced to have a large area, which greatly hinders the mass production and the commercial development of the biochip. Moreover, the EBL process has a high cost, resulting in further increased cost for the production of the ANA biochip.

The biochips provided by embodiments of the present disclosure include various types of biochips, and will be described below by taking a biochip based on an Anisotropic Nanofilter Array (ANA) (hereinafter, referred to as "ANA biochip") as an example.

As shown in FIGS. 1 to 4, the present embodiment provides a biochip including a guide layer 1, a channel layer 2, a plurality of nano channels 21, a plurality of micron channels 22, an encapsulation cover plate 3, and a driving unit 4.

Figure 2:
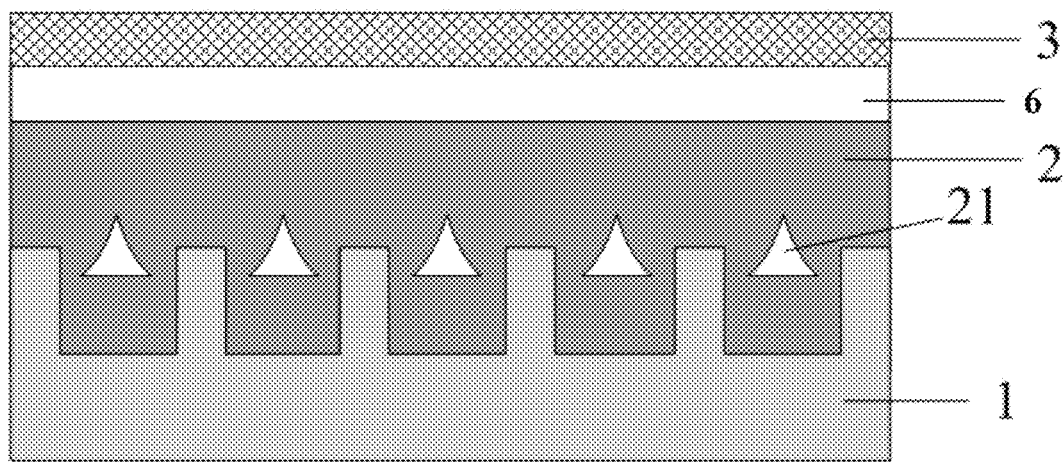
FIG. 2 is a schematic structural diagram (a cross-sectional view taken along a line A-B) of an implementation of a biochip according to an embodiment of the present disclosure.
Figure 3:
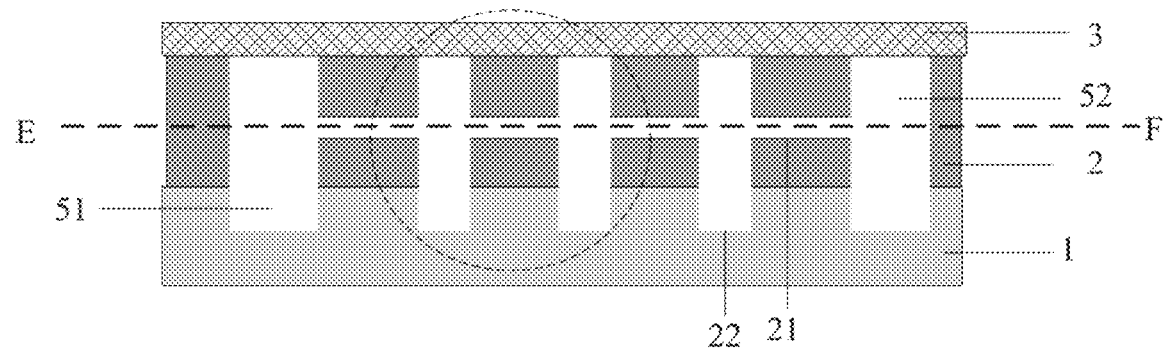
FIG. 3 is a schematic structural diagram (a cross-sectional view taken along a line C-D) of an implementation of a biochip according to an embodiment of the present disclosure.

It should be noted that FIG. 1 is a top view of the biochip provided by the present embodiment (with the encapsulation cover plate 3 being not shown); FIG. 2 is a cross-sectional view taken along a line A-B in FIG. 1; FIG. 3 is a cross-sectional view taken along a line C-D in FIG. 1 (with the driving unit 4 being not shown); and FIG. 4 is a cross-sectional view of the biochip in FIG. 1 in a plane that is parallel to a top surface of the encapsulation cover plate 3 and passes through a line E-F in FIG. 3.

Specifically, the channel layer 2 is disposed on the guide layer 1, and the channel layer 2 has therein a plurality of nano channels (which may also be referred to as first channels) 21 extending in a first direction. Each of the plurality of micron channels (which may also be referred to as second channels) 22 extends along a second direction. Each of the micron channels 22 is in communication with the plurality of nano channels 21, and may be disposed in a layer in which the channel layer 2 is disposed (i.e., disposed in the channel layer 2), or in a layer in which the channel layer 2 and the guide layer 1 are disposed. The encapsulation cover plate 3 is arranged on a side of the channel layer 2 distal to the guide layer 1. The driving unit 4 may be disposed on the encapsulation cover plate 3, and is configured to drive biomolecules to move. When the biomolecules are moved under the driving of the driving unit 4, different biomolecules are separated by the plurality of nano channels 21 and the plurality of micron channels 22.

It should be noted that the first direction and the second direction may be any directions, as long as the first direction is not parallel to the second direction. For example, as shown in FIG. 1, the first direction may be a horizontal direction S1, each of the nano channels 21 extends in the horizontal direction S1; and the second direction may be a vertical direction S2, each of the micron channels 22 extends in the vertical direction S2. Specifically, the first direction and the second direction may be set as needed, which is not limited herein.

Figure 4:
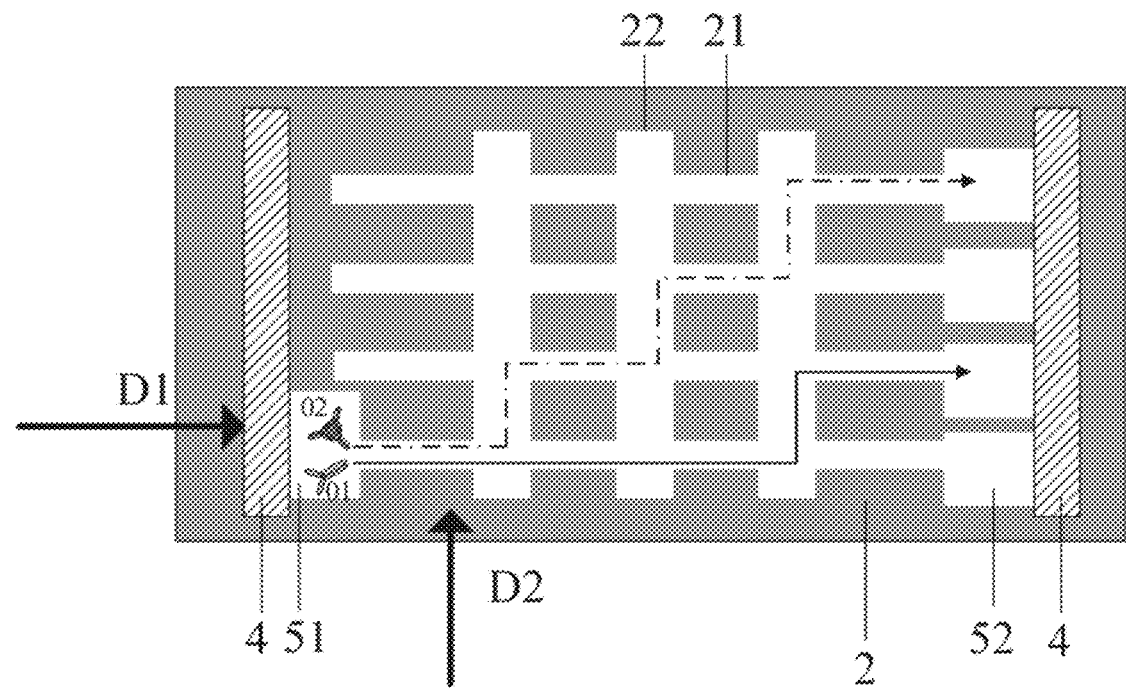
FIG. 4 is a cross-sectional view of the biochip of FIG. 1 in a plane that is parallel to a top surface of an encapsulation cover plate and passes through a line E-F in FIG. 3.

Specifically, referring to FIG. 4, the driving unit 4 provides a first driving force to drive the biomolecules to move from one end of the nano channels 21 to the other end of the nano channels 21, and a direction of the first driving force is approximately parallel to an extending direction of the nano channel 21. For example, the direction of the first driving force is D1 in FIG. 4. In addition, a lateral second driving force (which will be described in detail later) is also present in the ANA biochip provided by this embodiment, and a direction of the second driving force is not parallel to the direction of the first driving force. For example, the direction of the second driving force is D2 in FIG. 4. The second driving force drives the biomolecules to laterally move in the micron channels 22 during the movement of the biomolecules along the nano channels 21. Different biomolecules have different movement tracks during undergoing electrophoretic movement in the nano channels 21 and the micron channels 22. Referring to FIG. 4, for example, description will be made by taking two biomolecules having a same charge and a same volume but different masses as an example. A first biomolecule 01 with a smaller mass and a second biomolecule 02 with a larger mass undergo electrophoretic movement along the nano channels 21 under the action of the first driving force, and the first biomolecule 01 and the second biomolecule 02 move laterally in the respective micron channels 22 under the action of the second driving force. During the movement, the second biomolecule 02 stays in the nano channels 21 and the micron channels 22 for a longer time than the first biomolecule 01, such that the second driving force is applied to the second biomolecule 02 for a longer time, and a lateral displacement of the second biomolecule 02 is larger than that of the first biomolecule 01. In contrast, because the first biomolecule 01 stays in the nano channels 21 and the micron channels 22 for a shorter time, and thus the second driving force is applied to the first biomolecule 01 for a shorter time, such that the lateral displacement of the first biomolecule 01 is smaller. Therefore, the first biomolecule 01 and the second biomolecule 02 have different movement tracks during the movement from one end of the nano channels 21 to the other end of the nano channels 21, and the different biomolecules may be separated under the screening by the nano channels 21 and the micron channels 22.

It is noted that the different biomolecules include biomolecules having different characteristics such as sizes, masses, or charge quantities, which are not limited herein. The biomolecules includes various substances, for example, the biomolecules may be protein, DNA, etc., which is not limited herein.

Biomolecules are generally charged in a solvent. In the embodiments of the present disclosure, the biochip may separate biomolecules with a same kind of charges, and may separate biomolecules with different kinds of charges.

An electrostatic force between the charged molecules is much greater than a gravity of each of the molecules, so the biomolecules do not sink in a short time.

In an embodiment, the plurality of nano channels 21 may be disposed parallel to each other, and the plurality of micron channels 22 may also be disposed parallel to each other.

In an embodiment, the plurality of micron channels 22 have a same size in each direction.

In an embodiment, the plurality of nano channels 21 have a same size in each direction.

Further, as shown in FIGS. 1 and 4, in the ANA biochip provided by the present embodiment, the driving unit 4 may include a driving unit of each of various types, as long as it may drive different biomolecules to move. For example, the driving unit 4 may be a pair of separation electrodes, which are a first separation electrode (the left separation electrode in FIG. 1) and a second separation electrode (the right separation electrode in FIG. 1), respectively. The first separation electrode and the second separation electrode are respectively disposed at both ends of each of the nano channels 21. In an embodiment of the present disclosure, the biochip further includes a first liquid storage structure 51 and a plurality of second liquid storage structures 52. An orthographic projection (i.e., orthogonal projection) of the first separation electrode on the encapsulation cover plate 3 or the guide layer 1 at least partially overlaps an orthographic projection (i.e., orthogonal projection) of the first liquid storage structure 51 on the encapsulation cover plate 3 or the guide layer 1, and an orthographic projection of the second separation electrode on the encapsulation cover plate 3 or the guide layer 1 at least partially overlaps an orthographic projection of each of the plurality of second liquid storage structures 52 on the encapsulation cover plate 3 or the guide layer 1. One of the first separation electrode and the second separation electrode is connected to a power supply terminal, and the other one thereof is grounded. In this way, an electric field is generated between the first separation electrode and the second separation electrode. The first driving force is an electric field force. Different biomolecules move from one end of nano channels 21 to the other end of nano channels 21 under the driving of the electric field force.

Figure 5:
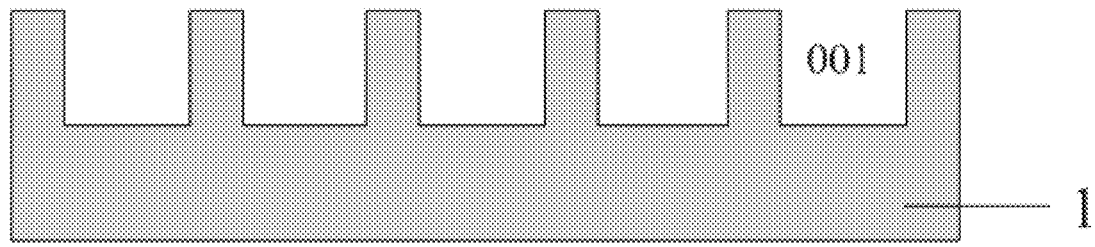
FIG. 5 is a schematic structural diagram (side view) of an implementation of a guide layer of a biochip according to an embodiment of the present disclosure.
Figure 6:
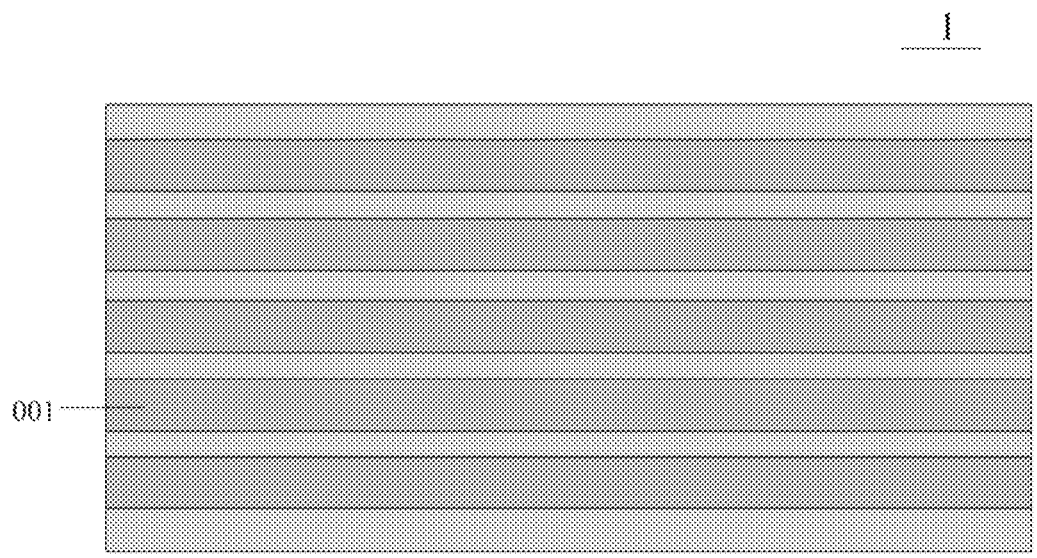
FIG. 6 is a schematic structural diagram (top view) of an implementation of a guide layer of a biochip according to an embodiment of the present disclosure.

Further, as shown in FIGS. 1 to 6, wherein FIG. 5 is a side view of the guide layer 1, and FIG. 6 is a top view of the guide layer 1. In the ANA biochip provided by the present embodiment, a plurality of first grooves 001 extending along the first direction may be provided at a side of the guide layer 1 proximal to the channel layer 2, and be configured to form the plurality of nano channels 21. Referring to FIGS. 1 to 4, the plurality of nano channels 21 are located in the channel layer 2, may specifically be a plurality of cavities extending along the first direction, and are in one-to-one correspondence with the first grooves 001 in the guide layer 1. An orthographic projection of each nano channel 21 on the guide layer 1 is located within an orthographic projection of a first groove 001 corresponding to the nano channel 21 on the guide layer 1. That is, each nano channel 21 is formed in the channel layer 2 at a position corresponding to each first groove 001. That is, one cavity extending along the first direction is formed in the channel layer 2 at the position corresponding to each first groove 001, and the cavity is the nano channel 21. The number of the first grooves 001 and the number of the nano channels 21 may be designed according to the requirement, which is not limited herein. A channel width of each of the nano channels 21 may be set according to a size of each of the biomolecules to be screened and separated, which is not limited herein. In embodiments of the present disclosure, each of the biomolecules to be screened and separated may have a diameter of less than 100 nm.

The nano channels 21 are directly formed in the channel layer 2, rather than being formed by attaching a cover plate to a base plate, thereby avoiding the following problems: collapses of the nano channels in the process of attaching the cover plate to the base plate; or the nano channels have a slit and the like due to an uneven attachment surface of the base plate and the cover plate, which affects the structural uniformity of the nano channels. Therefore, the ANA biochip provided by the present embodiment may be ensured to have the structural uniformity of the nano channels 21, and simplify the manufacturing process for the ANA biochip. For example, a manufacturing process related to the attaching of the base plate and the cover plate to each other is omitted.

Alternatively, a shape of a cross section of each nano channel 21 may include any shape such as a U-shape, a D-shape, a rectangle, a triangle, an ellipse, an ellipse-like shape, a circle, a semicircle, a square, a trapezoid, a pentagon, a hexagon, or another cross-sectional geometric structure. The geometric structure may be constant or may vary along a lengthwise direction of a micro channel (i.e., each nano channel 21 or each micron channel 22). Moreover, each nano channel 21 may have various arrangements or configurations, including linear, nonlinear, fused, branched, looped, twisted, stepped, etc., and may be designed specifically as desired, which is not limited herein.

Figure 7:
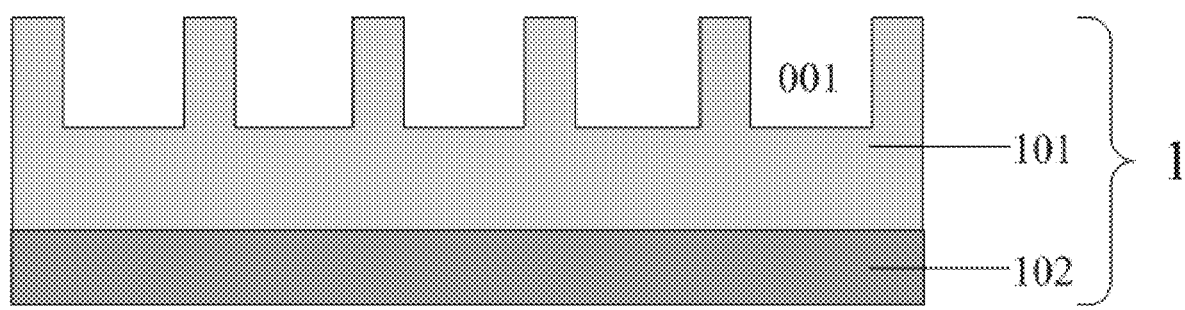
FIG. 7 is a schematic structural diagram (side view) of another implementation of a guide layer of a biochip according to an embodiment of the present disclosure.

Alternatively, as shown in FIG. 7, the guide layer 1 may have a one-piece structure, or may be formed by splicing at least two portions together. For example, the guide layer 1 may include a groove structure 101 and a base plate 102. A plurality of first grooves 001 extending along the first direction may be provided at a side of the groove structure 101 proximal to the channel layer 2. The base plate 102 is disposed on a side of the groove structure 101 distal to the channel layer 2. A surface area of a side of the base plate 102 contacting the groove structure 101 may be greater than or equal to a surface area of a side of the groove structure 101 distal to the channel layer 2. The materials of the base plate 102 and the groove structure 101 may be the same or different, and may be specifically designed according to needs, which is not limited herein.

Figure 8:
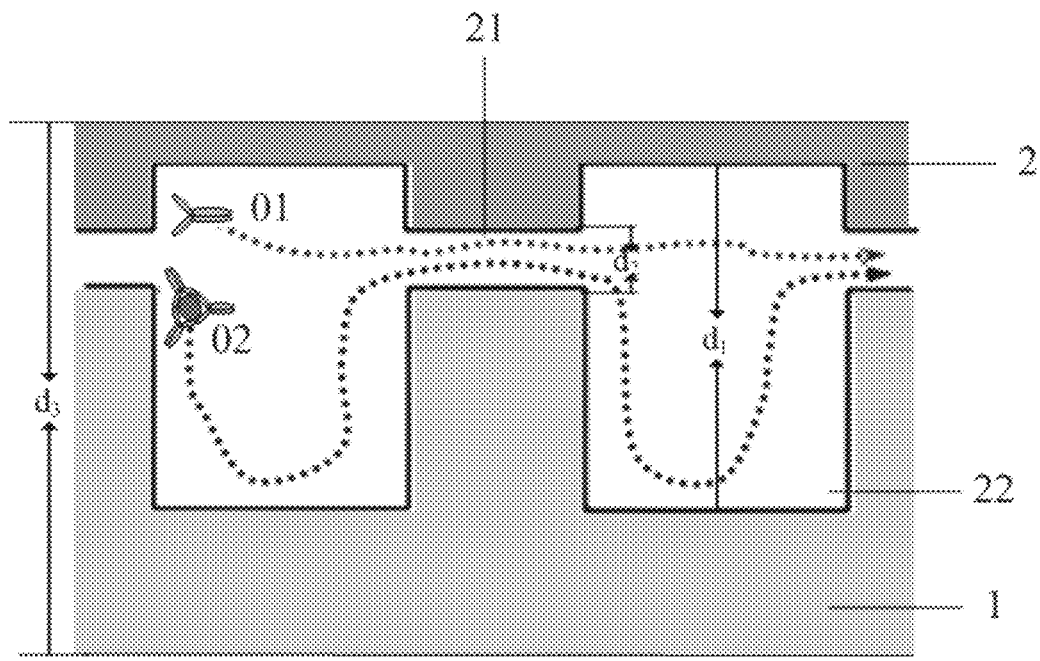
FIG. 8 is a partial schematic structural diagram (schematic diagram of a part of FIG. 3) of an implementation of a biochip according to an embodiment of the present disclosure.

Further, as shown in FIGS. 1, 3 and 8, wherein FIG. 8 is a partial schematic view of the channel layer 2 and the guide layer 1 shown in the dashed circle in FIG. 3. The ANA biochip provided by this embodiment includes a plurality of micron channels 22 extending along the second direction and communicating with each of the nano channels 21. Specifically, the plurality of micron channels 22 may be a plurality of second grooves, a height $d_1$ of each micron channel 22 (i.e. the second groove) is greater than a height $d_2$ of each nano channel 21, and the height $d_1$ of each micron channel 22 is less than a sum $d_3$ of heights of layers in which the channel layer 2 and the guide layer 1 are respectively located, as shown in FIG. 8. Referring to FIG. 8, description will be made by taking two biomolecules having the same charge and the same volume but different masses as an example. Specifically, during a first biomolecule 01 with a smaller mass and a second biomolecule 02 with a larger mass are driven by the driving unit 4 to undergo electrophoretic movement in the nano channels 21 and the micron channels 22, since the height $d_1$ of each micron channel 22 is greater than the height $d_2$ of each nano channel 21, the second biomolecule 02 with the larger mass will move deeper downward in the micron channels 22 than the first biomolecule 01 with the smaller mass, such that the time for which the second biomolecule 02 stays in the micron channels 22 will be further increased, and the time for which the lateral second driving force is applied to the second biomolecule 02 will be further increased, thereby further increasing a lateral displacement of the second biomolecule 02 through respective micron channels 22, and further increasing a difference between movement tracks of the first biomolecule 01 and the second biomolecule 02, which results in that the first biomolecule 01 and the second biomolecule 02 move into different second liquid storage structures 52, respectively. In this way, different biomolecules are separated more easily through the micron channels 21 and the nano channels 22. Alternatively, biomolecules with other different characteristics (e.g., charge quantities, sizes, etc.) may also be suitable for the above principle, which is not limited herein.

In embodiments of the present disclosure, the height $d_1$ of each micron channel 22 is on the order of several hundred microns. The height $d_2$ of each nano channel 21 is less than 200 nm, but is greater than a diameter of a biomolecule. In an embodiment of the present disclosure, each micron channel 22 is configured to have the height $d_1$, such that each micron channel 22 may store liquid and reduce a resistance of a biomolecule to travel in each nano channel along the first direction, such that respective biomolecules quickly pass through the nano channels.

Further, the ANA biochip provided by the present embodiment may or may not further include a planarization layer 6, which is disposed between the channel layer 2 and the encapsulation cover plate 3, as shown in FIG. 2. The planarization layer 6 is arranged on a butt joint surface (juncture) between the channel layer 2 and the encapsulation cover plate 3, such that a surface of the channel layer 2 proximal to the encapsulation cover plate 3 may be more flat, thereby improving the quality of attaching the encapsulation cover plate 3 and the channel layer 2 to each other. Moreover, the planarization layer 6 may increase the support force from the channel layer 2, and prevent the nano channels 21 in the channel layer 2 from being collapsed by the gravity of the encapsulation cover plate 3. On the other hand, if the material of the encapsulation cover plate 3 and the material of the channel layer 2 are unsuitable for attaching the encapsulation cover plate 3 and the channel layer 2 to each other, the planarization layer 6 may be added, and the encapsulation cover plate 3 and the channel layer 2 may be attached to each other with the planarization layer 6 by controlling the material of the planarization layer 6.

Further, as shown in FIGS. 1, 3 and 4, the ANA biochip provided by this embodiment may further include the first liquid storage structure 51 and the plurality of second liquid storage structures 52. The first liquid storage structure 51 is in communication with a first end of one or more of the nano channels 21, and is configured to store a mixed solution with unseparated biomolecules which are to be separated.

In particular, the first liquid storage structure 51 may be in communication with a first end of any one of the plurality of nano channels 21. Exemplarily, as shown in FIG. 1, the first liquid storage structure 51 is in communication with a first end of the nano channel 21 of the plurality of nano channels 21 that is located at the outermost (e.g., lowermost) side of the ANA biochip. The plurality of second liquid storage structures 52 are in one-to-one correspondence with and in communication with second ends of the plurality of nano channels 21, and are configured to store solutions with separated biomolecules, respectively. Under the driving of the driving unit 4, different biomolecules move from the first liquid storage structure 51 to the second liquid storage structures 52 together with the solution, are separated by the nano channels 21 and the micron channels 22. That is, different biomolecules have different movement tracks in movement, i.e. have different lateral displacements. Thus, different biomolecules enter different nano channels 21 as they are laterally displaced through the micron channels 22, and the second end of each nano channel 21 corresponds to one second liquid storage structure 52. Since among different biomolecules, a same kind of biomolecules having a same movement track enter a same nano channel 21, and then enter the second liquid storage structure 52 in communication with the corresponding nano channel 21 during the motion process, separated different biomolecules are stored in different second liquid storage structures 52, respectively.

Figure 9:
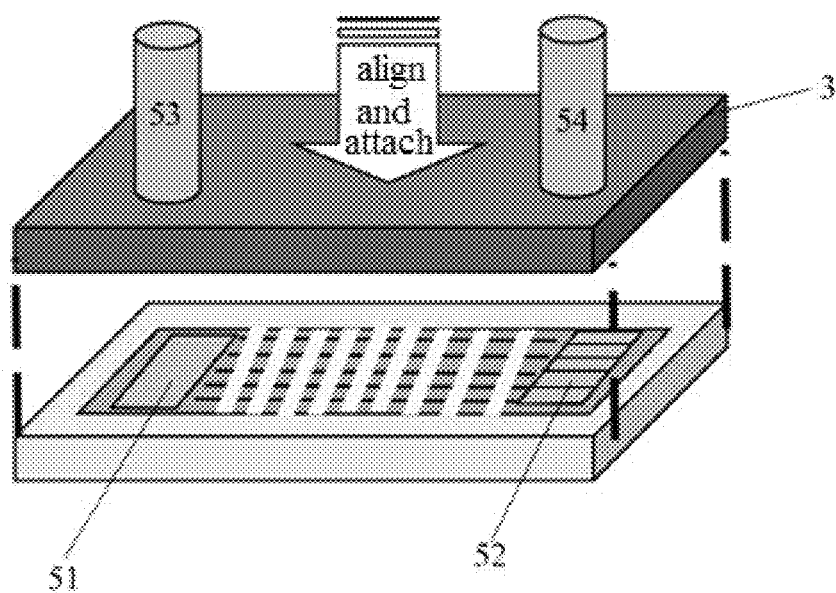
FIG. 9 is a schematic structural diagram of an encapsulation cover plate and a channel structure of a biochip according to an embodiment of the present disclosure.

Further, as shown in FIG. 9, the ANA biochip provided by this embodiment may further include a first capacity expansion structure 53 and a second capacity expansion structure 54, which may be respectively disposed on the encapsulation cover plate 3, for respectively expanding capacities of the first liquid storage structure 51 and the second liquid storage structures 52 for storing solutions. The specific structures and installation positions of the first capacity expansion structure 53 and the second capacity expansion structure 54 may be designed as needed, as long as the first capacity expansion structure 53 is connected to (e.g., in communication with) the first liquid storage structure 51, and the second capacity expansion structure 54 is connected to (e.g., in communication with) the second liquid storage structures 52, which is not limited herein.

Figure 10:
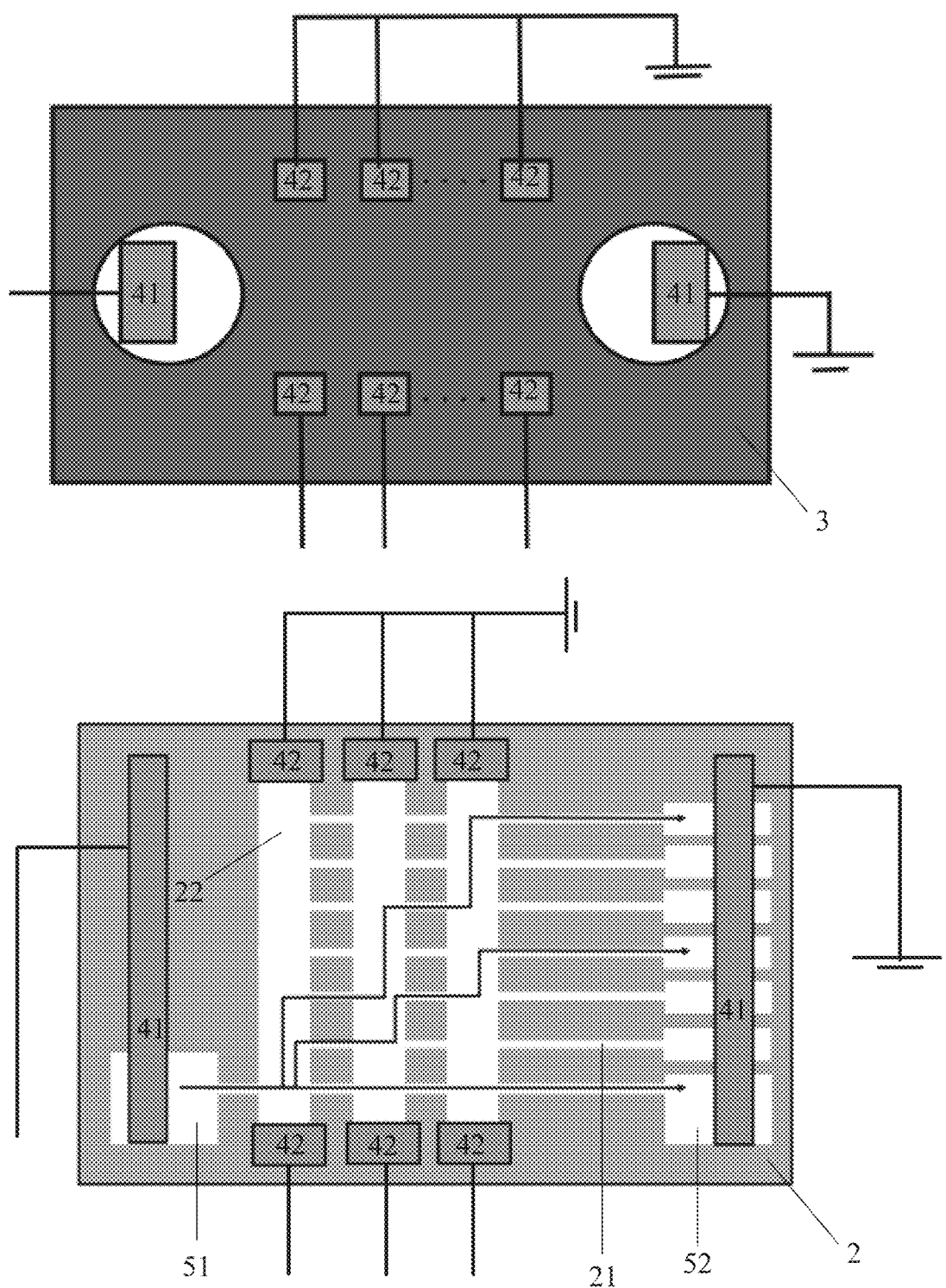
FIG. 10 is a schematic structural diagram of an implementation of a biochip according to an embodiment (a first embodiment) of the present disclosure.
Figure 11:
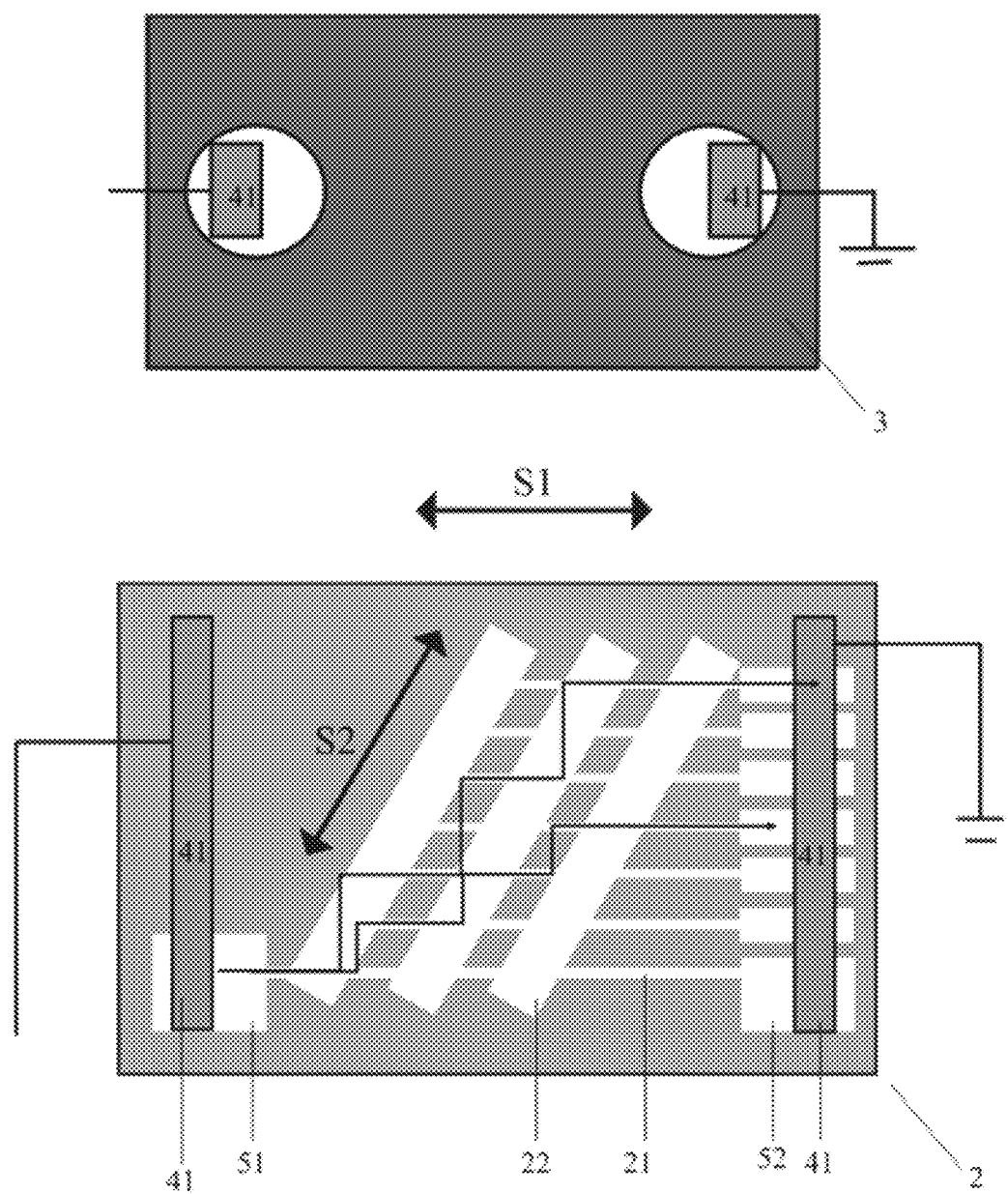
FIG. 11 is a schematic structural diagram of an implementation of a biochip according to an embodiment (a second embodiment) of the present disclosure.
Figure 12:
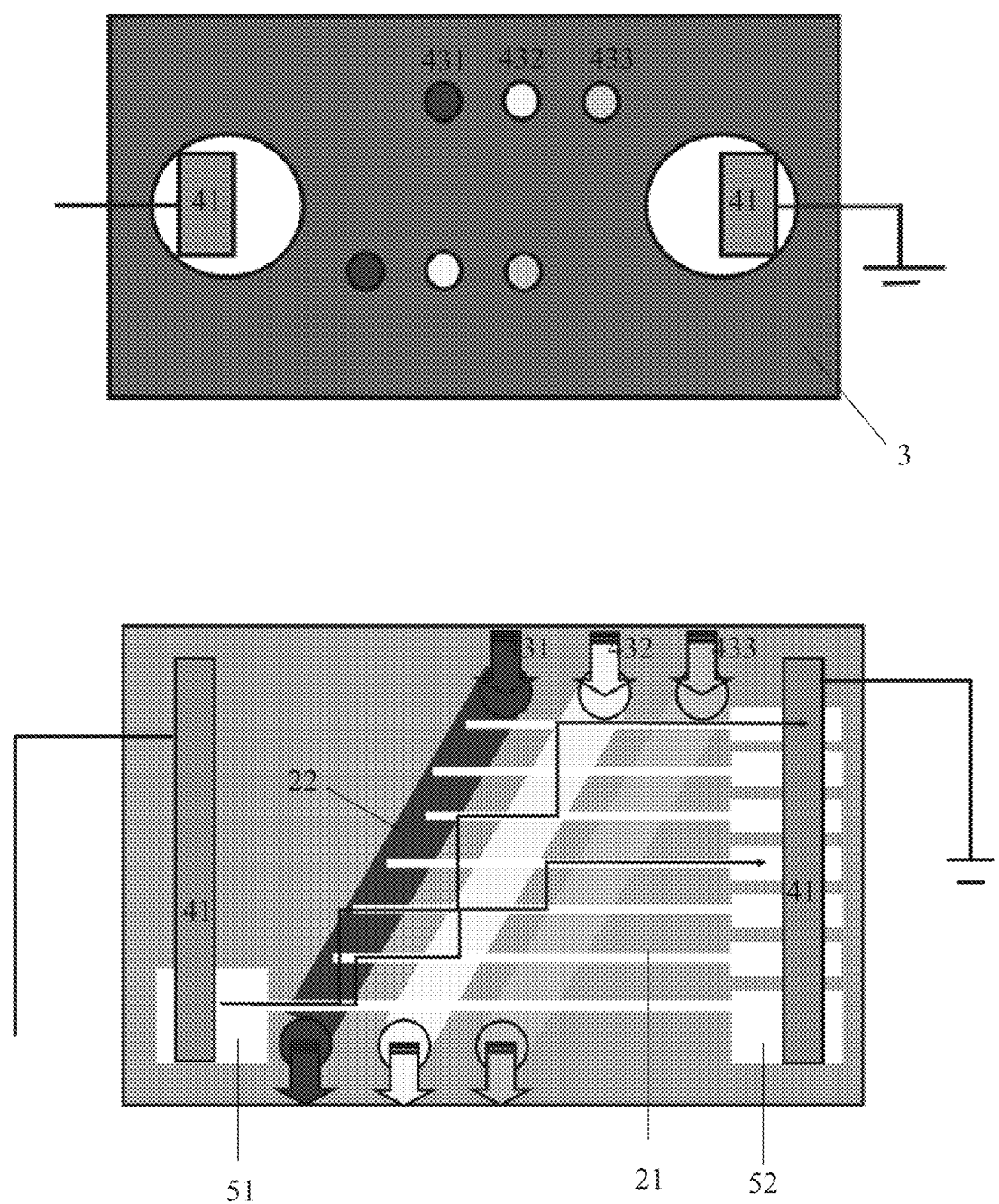
FIG. 12 is a schematic structural diagram of an implementation of a biochip according to an embodiment (a third embodiment) of the present disclosure.

Alternatively, as shown in FIGS. 10 to 12, in the ANA biochip provided by this embodiment, different biomolecules move from one end of the nano channels 21 to the other end of the nano channels 21 under the action of the first driving force provided by the driving unit 4. During the movement, the different biomolecules also need to be subjected to the second driving force, which causes the different biomolecules to laterally move, such that the different biomolecules enter into the different nano channels 21 through the micron channels 22. There are various manners to provide the second driving force, which will be described in the following first to third embodiments.

FIGS. 10 to 12 schematically show only a case where one of a pair of separation electrodes 41 is connected to a power supply and the other is grounded.

First Embodiment

As shown in FIG. 10, the driving unit of the ANA biochip is a pair of separation electrodes (e.g., first electrodes) 41 (e.g., the first separation electrode and the second separation electrode as described above), and the ANA biochip further includes a plurality of pairs of longitudinal driving electrodes (e.g., second electrodes) 42. The plurality of micron channels 22 and the plurality of nano channels 21 are orthogonal to each other.

Specifically, a pair of separation electrodes 41 are respectively disposed on the encapsulation cover plate 3 at positions corresponding to two ends of each nano channel 21, that is, positions on the encapsulation cover plate 3 corresponding to the first liquid storage structure 51 and the second liquid storage structures 52. One of the two separation electrodes 41 is connected to a power supply voltage, and the other separation electrode 41 is grounded, such that the electric field force (i.e., the first driving force) with a direction from the first liquid storage structure 51 to the second liquid storage structures 52 is generated between the two separation electrodes, so as to drive different biomolecules in the solution in the first liquid storage structure 51 to move along a direction from the nano channels 21 toward the second liquid storage structures 52. The number of the pairs of longitudinal driving electrodes 42 is equal to the number of the micron channels 22, each pair of longitudinal driving electrodes 42 includes two longitudinal driving electrodes 42, which are respectively disposed at two ends of the micron channel 22 corresponding to the pair of longitudinal driving electrodes 42. As shown in FIG. 10, a plurality of longitudinal driving electrodes 42 located on a same side of the pairs of longitudinal driving electrodes 42 are connected to a same power source, and a plurality of longitudinal driving electrodes 42 located on the other side are grounded, such that the electric field force (i.e., the second driving force) along an extending direction of each micron channel 22 is generated between the longitudinal driving electrodes located at the two ends of the micron channel 22, and causes different biomolecules to laterally move during the movement process, such that the different biomolecules enter into different nano channels 21 through the micron channels 22, and then enter into corresponding second liquid storage structures 52, thereby separating the different biomolecules from each other.

It should be noted that, the separation electrodes 41 and the longitudinal driving electrodes 42 may also be disposed in the channel layer 2; and positions where the separation electrodes 41 and the longitudinal driving electrodes 42 are disposed in the channel layer 2 correspond to positions where the separation electrodes 41 and the longitudinal driving electrodes 42 are disposed on the encapsulation cover plate 3. The separation electrodes 41 in the channel layer 2 are connected to the separation electrodes 41 on the encapsulation cover plate 3; and the longitudinal driving electrodes 42 in the channel layer 2 are connected to the longitudinal driving electrodes 42 on the encapsulation cover plate 3.

FIG. 10 schematically illustrates a case where the plurality of longitudinal driving electrodes 42 located on a same side of the pairs of longitudinal driving electrodes 42 are connected to a same power source and the plurality of longitudinal driving electrodes 42 on the other side are grounded. In the embodiment shown in FIG. 10, the electric field generated between each pair of longitudinal driving electrodes 42 is orthogonal to the electric field generated between the pair of separation electrodes 41. In the embodiment shown in FIG. 10, as shown in FIG. 10, the separation electrode 41 on the right side and the plurality of longitudinal driving electrodes 42 on the upper side are connected to a same potential (i.e., simultaneously connected to the power source or the ground), and the separation electrode 41 on the left side and the plurality of longitudinal driving electrodes 42 on the lower side are connected to a same potential (i.e., simultaneously connected to the ground or the power source). That is, in the embodiment shown in FIG. 10, as shown in FIG. 10, the separation electrode 41 on the right side and the plurality of longitudinal driving electrodes 42 on the upper side are connected to a same first potential (i.e., simultaneously connected to the power source or the ground), while the separation electrode 41 on the left side and the plurality of longitudinal driving electrodes 42 on the lower side are connected to a same second potential (i.e., simultaneously connected to the ground or the power source). In an embodiment, the first potential is a power supply voltage, the second potential is a ground potential, and vice versa.

In an embodiment of the present disclosure, respective electrodes may be in direct contact with the solution in a large area to reduce contact resistance.

Second Embodiment

As shown in FIG. 11, the driving unit of the ANA biochip is a pair of separation electrodes 41. The plurality of micron channels 22 are obliquely arranged with respect to the plurality of nano channels 21.

Specifically, the plurality of nano channels 11 are arranged along a first direction S1, the plurality of micron channels 22 are arranged along a second direction S2, the second direction S2 and the first direction S1 are not parallel and not perpendicular to each other. That is, an angle between an extending direction of each micron channel 22 and an extending direction of each nano channel 21 is less than 90°. A pair of separation electrodes 41 are respectively disposed on the encapsulation cover plate 3 at positions corresponding to two ends of each nano channel 21, that is, positions on the encapsulation cover plate 3 corresponding to the first liquid storage structure 51 and the second liquid storage structures 52. One of the two separation electrodes 41 is connected to a power supply voltage, and the other separation electrode 41 is grounded, such that the electric field force (i.e., the first driving force) with a direction from the first liquid storage structure 51 to the second liquid storage structures 52 is generated between the two separation electrodes, so as to drive different biomolecules in the solution in the first liquid storage structure 51 to move along a direction from the nano channels 21 toward the second liquid storage structures 52. Since the plurality of micron channels 22 are obliquely arranged with respect to the plurality of nano channels 21, when different biomolecules move in the nano channels 21, channel walls of the oblique micron channels 22 generate a lateral second driving force causing different biomolecules to laterally move during the movement process, and therefore, the different biomolecules enter into different nano channels 21 through the micron channels 22, and then enter into corresponding second liquid storage structures 52, thereby separating the different biomolecules from each other.

It should be noted that the separation electrodes 41 may also be disposed in the channel layer 2, and positions where the separation electrodes 41 are disposed in the channel layer 2 correspond to positions where the separation electrodes 41 are disposed on the encapsulation cover plate 3. The separation electrodes 41 in the channel layer 2 are connected to the separation electrodes 41 on the encapsulation cover plate 3, respectively.

Third Embodiment

As shown in FIG. 12, the driving unit of the ANA biochip is a pair of separation electrodes 41. The plurality of micron channels 22 are obliquely arranged with respect to the plurality of nano channels 21, and different biological reaction reagents are provided in different micron channels 22, respectively. Description will be made below by taking an example in which a biomolecule is an antigen and a biological reaction reagent is an antibody solution.

Specifically, a pair of separation electrodes 41 are respectively disposed on the encapsulation cover plate 3 at positions corresponding to two ends of each nano channel 21, that is, positions on the encapsulation cover plate 3 corresponding to the first liquid storage structure 51 and the second liquid storage structures 52. One of the two separation electrodes 41 is connected to a power supply voltage, and the other separation electrode 41 is grounded, such that the electric field force (i.e., the first driving force) with a direction from the first liquid storage structure 51 to the second liquid storage structures 52 is generated between the two separation electrodes, so as to drive different biomolecules in the solution in the first liquid storage structure 51 to move along a direction from the nano channels 21 toward the second liquid storage structures 52.

Further, the plurality of nano channels 21 are arranged along a first direction S 1, the plurality of micron channels 22 are arranged along a second direction S2, and the second direction S2 and the first direction Si are not parallel and not perpendicular to each other. That is, an angle between an extending direction of each micron channel 22 and an extending direction of each nano channel 21 is less than 90°. Since the plurality of micron channels 22 are obliquely arranged with respect to the plurality of nano channels 21, when different antigens move in the nano channels 21, channel walls of the oblique micron channels 22 generate a lateral second driving force. Different antibody solutions (e.g., a first antibody solution 431, a second antibody solution 432 and a third antibody solution 433 shown in FIG. 12) are provided in different micron channels 22, respectively. Each antigen and the corresponding antibody are contacted, which will cause a specific reaction therebetween. That is, the antigen is combined with corresponding antibody molecule, such that a volume and a mass of the antigen are changed. Therefore, different antigens may be differentiated into antigen molecules with different masses and volumes after contacting the corresponding antibody solutions in different micron channels 22 and therefore, causing the specific reaction therebetween, such that under the driving of the second driving force, different antigen molecules laterally move during the movement process, and therefore, the different antigen molecules enter into different nano channels 21 through the micron channels 22, and then enter into corresponding second liquid storage structures 52, thereby separating the different antigen molecules from each other.

It should be noted that the separation electrodes 41 may also be disposed in the channel layer 2, positions where the separation electrodes 41 are disposed in the channel layer 2 correspond to positions where the separation electrodes 41 are disposed on the encapsulation cover plate 3. The separation electrodes 41 in the channel layer 2 are connected to the separation electrodes 41 on the encapsulation cover plate 3, respectively.

It should be noted that solution inlets may be provided in the encapsulation cover plate 3, and each of the solution inlets corresponds to each biological reaction reagent (e.g. antibody solution), and is provided on the encapsulation cover plate 3 at positions corresponding to each of two ends of each micron channel 22.

In another embodiment, the first antibody solution 431, the second antibody solution 432 and the third antibody solution 433 may be mixed together. When a plurality of antigen molecules contact the above mixed antibody solutions, some antigen molecules react with the antigen molecules and thus, cannot continue to travel in the nano channels, and the unreacted antigen molecules reach the second liquid storage structures 52 through the nano channels, so as to screen and separate the antigen molecules.

In some embodiments, each of the plurality of micron channels (i.e., second channels) 22 has a height on the order of several hundred microns, and each of the plurality of nano channels (i.e., first channels) has a height of less than 200 nm.

In some embodiments, the plurality of first channels 21 are disposed to be spaced apart from each other along the second direction S2, and the plurality of second channels 22 are disposed to be spaced apart from each other along the first direction S1.

In some embodiments, a dimension of each of the plurality of first channels 21 in a direction perpendicular to the first direction is larger than a diameter of each of the biomolecules (e.g., in a case where each biomolecule is not spherical, the diameter of the biomolecule may refer to the largest dimension among dimensions of the biomolecule in various directions).

In some embodiments, a dimension of each of the plurality of second channels 22 in a direction perpendicular to the second direction S2 is larger than a diameter of each of the biomolecules.

In some embodiments, an angle between the first direction Si and the second direction S2 is an acute angle, in which case, the driving unit 4 of the biochip may include only the first separation electrode 41 and the second separation electrode 41, as shown in FIGS. 11 and 12.

In some embodiments, the first direction Si and the second direction S2 are perpendicular to each other, and the driving unit 4 may further include a plurality of sets of driving electrodes (e.g., a plurality of sets of longitudinal driving electrodes 42) in one-to-one correspondence with the plurality of second channels (i.e., micron channels 22) in addition to the first separation electrode 41 and the second separation electrode 41. Further, the first separation electrode 41 and the second separation electrode 42 are disposed along the first direction S1, and each set of the plurality of sets of driving electrodes includes two driving electrodes 42 disposed along the second direction S2 and respectively located at both ends of a corresponding second channel (i.e., micron channel 22), as shown in FIGS. 1 and 10.

Figure 13:
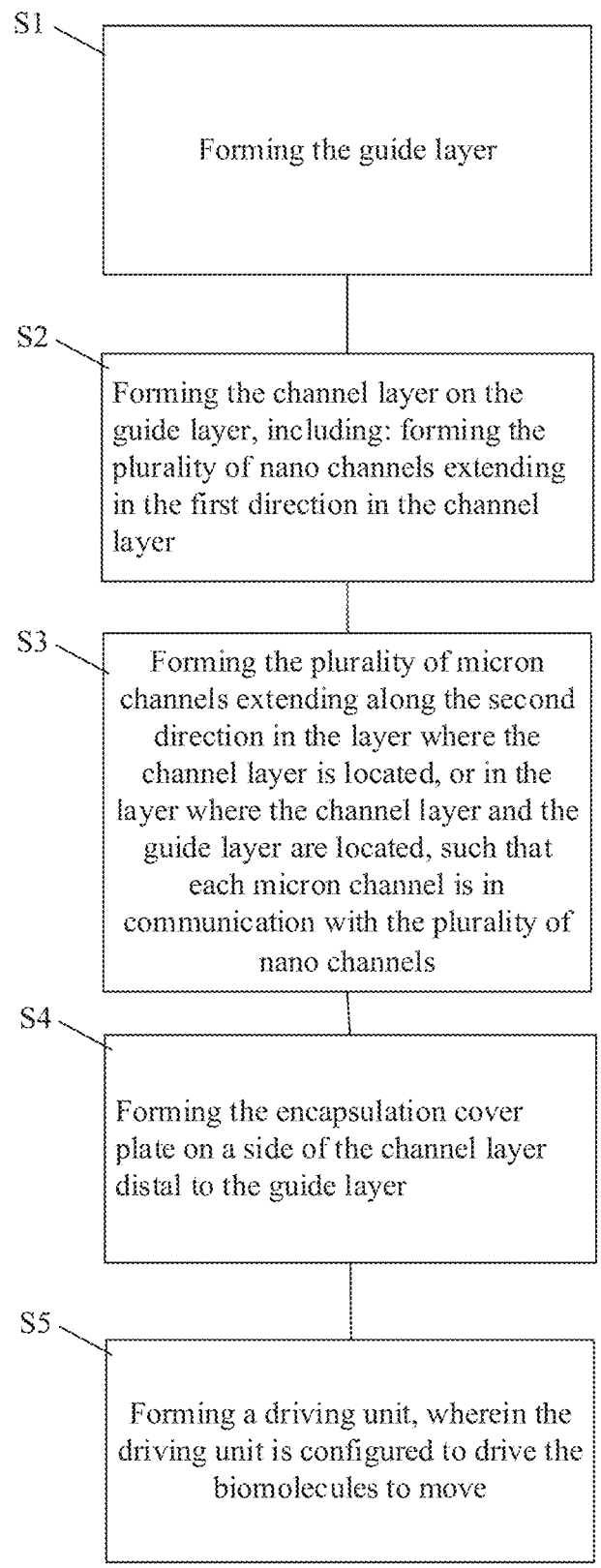
FIG. 13 is a flowchart of an implementation of a method for manufacturing a biochip according to an embodiment of the present disclosure.

Correspondingly, as shown in FIG. 13, the present embodiment further provides a method for manufacturing a biochip based on an anisotropic nanofilter array, and the method includes the following steps S1 to S5.

Step S1 includes forming the guide layer 1.

Specifically, a material layer of the guide layer 1 is first formed, and then, a plurality of first grooves 001 extending along the first direction are formed on a side of the material layer of the guide layer 1 proximal to the channel layer 2.

Alternatively, referring to FIGS. 5 and 7, the guide layer 1 may have a one-piece structure, or may be formed by splicing at least two parts together. Referring to FIG. 5, if the guide layer 1 has a one-piece structure, the plurality of first grooves 001 are directly formed on the side of the guide layer 1 proximal to the channel layer 2. Referring to FIG. 7, if the guide layer 1 is formed by splicing at least two parts together, for example, the guide layer 1 is formed by splicing the base plate 102 and a groove structure 101 together, the base plate 102 is formed firstly, and then, the groove structure 101 is formed. The grooves 101 are formed on a side of the groove structure 101 proximal to the channel layer 2, and then the groove structure 101 is combined with the base plate 102. The materials of the base plate 102 and the groove structure 101 may be the same or different, and may be specifically designed according to needs, which is not limited herein.

In embodiments of the present disclosure, the height $d_1$ of each micron channel 22 is on the order of several hundred microns. The height $d_2$ of each nano channel 21 is less than 200 nm, but is greater than a diameter of a biomolecule. A height of the encapsulation cover plate 3 is on the order of a centimeter and a height of the base plate 102 is on the order of a millimeter, such that the electric field in which the molecules are subjected to an electric field force may be considered as a parallel unidirectional electric field.

In embodiments of the present disclosure, the base plate 102 may be a silicon or glass base plate.

Further, the plurality of first grooves 001 extending along the first direction are formed on the side of the guide layer 1 proximal to the channel layer 2, by a photolithography process, an electron beam lithography process, a nano-imprinting process, an etching process (e.g., a dry etching process), a thermal etching process, or a combination thereof. For example, the material layer of the guide layer 1 is formed firstly, and then, the side of the guide layer 1 proximal to the channel layer 2 is etched according to a shape of each first groove 001. Depending on the application of the nano channels 21 and micron channels 22, the guide layer 1 may be made of various suitable materials, including an insulating material, a semiconductor material, a conductive material, or a combination thereof.

Step S2 includes forming the channel layer 2 on the guide layer 1, including: forming the plurality of nano channels 21 extending in the first direction in the channel layer 2.

Specifically, the channel layer 2 may be formed on the guide layer 1 through a thin film deposition process, and the plurality of nano channels 21 extending along the first direction are formed in the channel layer 2. The material of the channel layer 2 is a thin film deposition material suitable for the thin film deposition process. The thin film deposition process may include various processes, such as a sputtering method (e.g., magnetron sputtering method) and an evaporation method (e.g., a chemical vapor deposition method, a plasma enhanced chemical vapor deposition (PECVD) method, a thermal vapor deposition method, an atomic layer deposition (ALD) method, and an electron beam evaporation method). Alternatively, description will be made by taking an example in which the material of the channel layer 2 is deposited by the sputtering method.

Further, step S2 may specifically include the following steps.

The channel layer 2 is formed on the guide layer 1 through the thin film deposition process, during which a plurality of cavities which are the nano channels and correspond to the plurality of first grooves 001 one by one are formed in the channel layer 2 at the positions corresponding to the first grooves 001, by means of different deposition rates of the material of the channel layer 2 at a convex portion and a concave portion of the first groove 001 in the guide layer 1.

Figure 14:
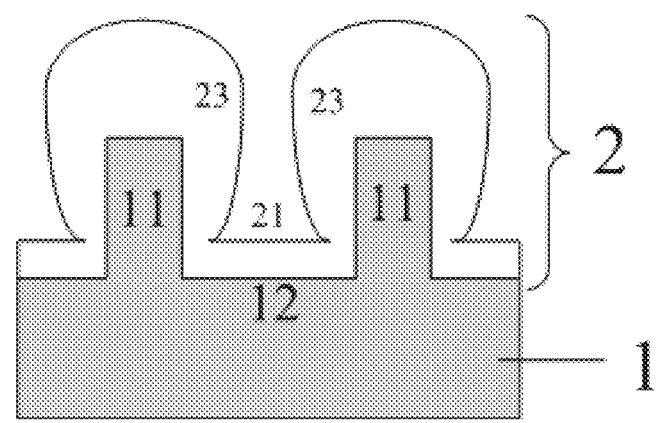
FIG. 14 is a schematic diagram of an implementation of a method for manufacturing a nano channel of a biochip according to an embodiment of the present disclosure.
Figure 15:
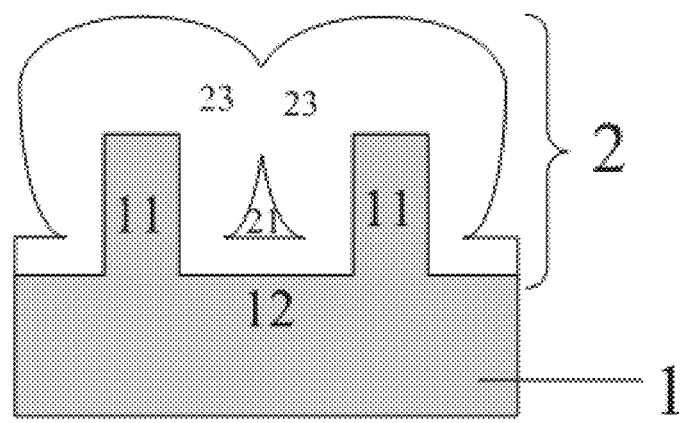
FIG. 15 is a schematic diagram of another implementation of a method for manufacturing a nano channel of a biochip according to an embodiment of the present disclosure.

Specifically, referring to FIGS. 14 and 15, a partial schematic view of one first groove 001 in the guide layer 101 is taken as an example for explanation. Each first groove 001 has a recess 12 and humps 11 located at both sides of the recess 12. During a thin film deposition process, a deposition rate of a thin film deposition material forming the channel layer 2 at each hump 11 of the first groove 001 is greater than a deposition rate of the thin film deposition material at the recess 12 of the first groove 001. For example, in a case where the material of the channel layer 2 is deposited by a sputtering method, when the thin film deposition material is sputtered onto the guide layer 1, the thin film deposition material is continuously accumulated on and around the humps 11 of the first groove 001, such that two protrusions 23 are formed on the two humps 11, respectively. A width of a cross section of each protrusion 23 is continuously increased and a distance between the two protrusions 23 is continuously decreased as the time of sputtering increases, such that a cavity which is one of the nano channels 21 is formed in the channel layer 2. The thin film deposition material accumulated at the recess 12 of the first groove 001 serves as a bottom surface of the nano channel 21 and the two protrusions 23 accumulated at the humps 11 of the first groove 001 serve as sidewalls of the nano channel 21, which defines the nano channel 21, such that the current method avoids the need for developing suitable etchants for a variety of different micron channel materials, respectively. The current method is applicable to the formation of nano channels 21 using a variety of suitable materials.

Further, referring to FIGS. 14 and 15, the top of each of the nano channels 21 may be open (as shown in FIG. 14) or closed (as shown in FIG. 15), and a size and a shape of each of the nano channels 21 may also be varied by controlling the duration or power for sputtering the thin film deposition material. For example, a longer sputtering time or a higher sputtering power causes each protrusion 23 to be larger and the distance between two protrusions 23 to be smaller, such that the size of each of the nano channels 21 becomes smaller. A whole nano channel 21 may be formed in the channel layer 2 by forming the first groove 001 on the guide layer 1 directly through a film deposition method. The nano channel may be formed without attaching the base plate to the cover plate, thereby avoiding the following problems: the nano channel collapses in the process of attaching the cover plate to the base plate, and/or the nano channel has a slit and the like due to the uneven attachment surfaces of the base plate and the cover plate, which affect the structural uniformity of the nano channel. Therefore, the ANA biochip provided by the present embodiment may ensure the structural uniformity of the nano channel 21, and simplify the manufacturing process for the ANA biochip. For example, the manufacturing process related to attaching the base plate and the cover plate to each other is omitted. Further, etching the nano channel 21 with a high precision is not required, such that the difficulty of processes for the ANA biochip is reduced.

Alternatively, the thin film deposition material forming the channel layer 2 and the nano channels 21 in the channel layer 2 include, but are not limited to: polymeric materials such as silicone polymers (e.g., polydimethylsiloxanes and epoxy polymers), polyimides, polycarbonates, polyesters, polyamides, polyethers, polyurethanes, polyfluorocarbons, fluorinated polymers (e.g., polyvinyl fluoride, polyvinylidene fluoride, polytetrafluoroethylene, polychloro trifluoroethylene, perfluoro alkoxyl alkane resin, fluoro ethylene-propylene, polyethylene tetrafluoroethylene, polyethylene trifluoro ethylene chloride, perfluoropolyethers, perfluoro sulfonic acid, perfluoro polyoxy heterocycle butane, FFPM/FFKM (perfluorinated elastomer [perfluoro elastomer]), FPM/FKM (fluorocarbon [chlorotrifluoroethylene vinylidene fluoride]), and copolymers thereof), polyether ether ketones (PEEK), polystyrene, poly (acrylonitrile butadiene styrene) (ABS), acrylates, and acrylic polymers (e.g., polymethylmethacrylate), and other substituted and unsubstituted polyolefins (e.g., cycloolefin polymers, polypropylene, polybutene, polyethylene (PE, e.g., crosslinked PE, high density PE, medium density PE, linear low density PE, low density PE, or ultra high molecular weight PE), polymethylpentene, polybutene-1, polyisobutylene, ethylene propylene rubber, ethylene propylene diene monomer (M grade) rubber), and copolymers thereof (e.g., cycloolefin copolymers); ceramics such as alumina, silica, zirconia, and the like; semiconductors such as silicon, gallium arsenide, and the like; glass; a metal; and coating compositions, composites (e.g., bulk composites of any one of the materials described herein), and laminates thereof (e.g., composite materials formed from several different adhesive layers of the same or different materials, such as polymer laminates or polymer-metal laminates, e.g., copper-coated polymers, ceramic-in-metal, or polymer-in-metal composites).

Step S3 includes forming the plurality of micron channels 22 extending along the second direction in the layer where the channel layer is located, or in the layer where the channel layer and the guide layer are located, such that each micron channel 22 is in communication with the plurality of nano channels 21.

Specifically, the plurality of second grooves which extend in the second direction and are in communication with each nano channel 21 are formed in the layer where the channel layer is located, or in the layer where the channel layer and the guide layer are located, by using a mask corresponding to the pattern of the micron channels 21, through an etching process, and the second grooves are the micron channels 22. That is, after the nano channels 21 are formed, a patterning process for the micron channels 22 is performed on the channel layer 2 according to the desired pattern of the micron channels 22 and the desired height of each of the micron channels 22. The height of each of the micron channels 22 is greater than the height of each of the nano channels 21 and less than the sum of the heights of the channel layer 2 and the guide layer 1, as shown in FIG. 8.

Optionally, the ANA biochip provided by this embodiment further includes the first liquid storage structure 51 and the plurality of second liquid storage structures 52. The first liquid storage structure 51 and the second liquid storage structures 52 may be formed together with the micron channels 22 in a same step. That is, the patterns of the first liquid storage structure 51 and the second liquid storage structures 52 are incorporated into the pattern for etching the micron channels 22.

Step S4 includes forming the encapsulation cover plate 3 on a side of the channel layer 2 distal to the guide layer 1.

Specifically, referring to FIG. 9, the encapsulation cover plate 3 may be made of any material. After the encapsulation cover plate 3 is formed, the encapsulation cover plate 3 and the channel structure (including the channel layer 2 and the guide layer 1) are aligned with each other and assembled to form the ANA biochip. In the present embodiment of the present disclosure, the encapsulation cover plate 3 may include an organic polymer such as polydimethylsiloxane (PDMS) and has a height of 1 cm.

Optionally, the method may further include a step of forming the planarization layer 6 between steps S3 and S5. After the micron channels 22 are patterned, the planarization layer 6 is disposed on the channel layer 2, and the planarization layer 6 is patterned according to an opening of each of the micron channels 22. Then, the encapsulation cover plate 3 and the channel structure with the planarization layer 6 are aligned with each other and assembled, and then, are encapsulated.

Step S5 includes forming a driving unit 4, wherein the driving unit 4 is configured to drive the different biomolecules to move, and when the different biomolecules move under the driving of the driving unit 4, the different biomolecules are separated through the nano channels 21 and the micron channels 22.

Specifically, the driving unit 4 may be a pair of separation electrodes. Since the nano channels 21 of the ANA biochip provided by the present embodiment are directly formed in the channel layer 2, the separation electrodes may be formed on a side of the encapsulation cover plate 3 proximal to the channel layer 2. The separation electrodes do not affect the leakproofness of the nano channels 21, so the separation electrodes may be disposed on the encapsulation cover plate.

Further, the material of the guide layer 1 may include each of a plurality of materials, for example, may include a glass material. Since the ANA biochip provided by this embodiment is manufactured by the above manufacturing process. For example, the nano channels 21 are formed by using a thin film deposition method, and the micron channels 22 are formed by using an etching method. In this way, the process flows used in this embodiment may be adopted to form corresponding elements on a large-area glass substrate, so as to solve the following problems in the prior art that the ANA biochip is manufactured by using a silicon process: the ANA biochip having a large area cannot be manufactured due to the limitation of the area and the etching precision of the silicon chip.

It should be understood that the above embodiments are merely exemplary embodiments adopted to explain the principles of the present disclosure, and the present disclosure is not limited thereto. It will be apparent to one of ordinary skill in the art that various changes and modifications may be made therein without departing from the scope of the present disclosure as defined by the appended claims, and such changes and modifications also fall within the scope of the present disclosure.

What is claimed is:

1. A biochip comprising:
   a guide layer;
   a channel layer on the guide layer, the channel layer having within the channel layer a plurality of first channels extending in a first direction, each first channel of the plurality of first channels projecting a first orthographic projection onto the guide layer;
   a plurality of second channels extending in a second direction, wherein each of the plurality of second channels is in communication with the plurality of first channels, and wherein the plurality of second channels is disposed in a first layer where the channel layer is located, or is disposed in a second layer where the channel layer and the guide layer are located;
   an encapsulation cover plate on a side of the channel layer distal to the guide layer;
   a driving unit configured to drive biomolecules to move;
   a plurality of first grooves, each first groove of the plurality of first grooves projecting a second orthographic projection onto the guide layer wherein the plurality of first grooves extending along the first direction are disposed on a side of the guide layer proximal to the channel layer, and have a one-to-one correspondence with the plurality of first channels, and the first orthographic projection of each first channel of the plurality of first channels on the guide layer is within the second orthographic projection of a corresponding first groove of the plurality of first grooves on the guide layer.

2. The biochip of claim 1, wherein the plurality of second channels comprises a plurality of second grooves, and is in a third direction perpendicular to both the first direction and the second direction, each second groove of the plurality of second groove has a first height and each first channel of the plurality of first channels has a second height wherein the first height is larger than the second height of each of the plurality of first channels, and the first height is smaller than a sum of heights of the first layer where the channel layer is located and of a third layer where the guide layer is located.

3. The biochip of claim 1, further comprising:
   a planarization layer disposed between the channel layer and the encapsulation cover plate.

4. The biochip of claim 1, further comprising:
   a first liquid storage structure in communication with at least a first end of a first channel of the plurality of first channels and configured to store a mixed solution having unseparated biomolecules; and
   a plurality of second liquid storage structures in a one-to-one correspondence with and in communication with second ends of the plurality of first channels, respectively, and configured to store solutions having separated biomolecules, respectively.

5. The biochip of claim 4, wherein the plurality of first channels are arranged side by side along the second direction, and the first liquid storage structure is in communication with a first end of a first channel of the plurality of first channels arranged along the second direction.

6. The biochip of claim 4, wherein the driving unit comprises a first separation electrode and a second separation electrode, the first separation electrode projecting a third orthographic projection onto the guide layer, the first liquid storage structure projecting a fourth orthographic projection onto the guide layer, the second separation electrode projecting a fifth orthographic projection onto the quide layer, the plurality of second liquid storage structures projecting a sixth orthographic projection onto the quide layer wherein the third orthographic projection at least partially overlaps the fourth orthographic projection, and the fifth orthographic projection at least partially overlaps the sixth orthographic projection.

7. The biochip of claim 2, wherein each second channel of the plurality of second channels has a height greater than or equal to 100 microns, and each first channel of the plurality of first channels has a height less than 200 nm.

8. The biochip of claim 1, wherein each first channel of the plurality of first channels are separated from each other along the second direction, and each second channel of the plurality of second channels are separated from each other along the first direction.

9. The biochip of claim 1, wherein each first channel of the plurality of first channels has a first dimension in a direction perpendicular to the first direction and each biomolecule of the biomolecules has a second diameter wherein the first diameter is greater than the second diameter.

10. The biochip of claim 1, wherein each second channel of the plurality of second channel has a third dimension in a direction perpendicular to the second direction and each biomolecule of the biomolecules has a second diameter wherein the third diameter is greater than the second diameter.

11. The biochip of claim 1, wherein the first direction and the second direction form an acute angle between the first direction and the second direction.

12. The biochip of claim 6, wherein the first direction is perpendicular to the second direction, and the driving unit further comprises a plurality of sets of driving electrodes in a one-to-one correspondence with the plurality of second channels;
the first separation electrode and the second separation electrode are arranged along the first direction; and
each set of the plurality of sets of driving electrodes comprises two driving electrodes arranged along the second direction and respectively at both ends of a corresponding second channel.

13. A method of manufacturing a biochip, the method comprising:
forming a guide layer;
forming a channel layer on the guide layer, wherein the forming the channel layer on the guide layer comprises:
forming a plurality of first channels extending in a first direction in the channel layer;
forming a plurality of second channels extending along a second direction in a first layer where the channel layer is located, or in a second layer where the channel layer and the guide layer are located, such that each second channel of the plurality of second channels is in communication with the plurality of first channels;
forming an encapsulation cover plate on a side of the channel layer distal to the guide layer; and
forming a driving unit configured to drive biomolecules to move;
the method further comprising forming a plurality of first grooves extending along the first direction on a side of the guide layer proximal to the channel layer, and in a one-to-one correspondence with the plurality of first channels such that an orthographic projection of each channel of the plurality of first channels on the guide layer is within an orthographic projection of a corresponding groove of the plurality of first grooves on the guide layer.

14. The method of claim 13, wherein the forming the channel layer on the guide layer comprises:
forming a channel layer on the guide layer by way of a thin film deposition process.

15. The method of claim 13, wherein the forming the guide layer comprises:
forming the guide layer using a material;
forming the plurality of first grooves extending along the first direction on the side of the guide layer proximal to the channel layer; and wherein
the forming the channel layer on the guide layer comprises: forming the plurality of first channels in a one-to-one correspondence with the plurality of first grooves in the channel layer at positions corresponding to the plurality of first grooves, as a result of deposition rates of a material of the channel layer at humps of the plurality of first grooves being different from recesses of the plurality of first grooves during the forming the channel layer on the guide layer by way of a thin film deposition process.

16. The method of claim 15, wherein the forming the plurality of first grooves extending along the first direction on the side of the guide layer proximal to the channel layer comprises:
forming the plurality of first grooves extending along the first direction on the side of the guide layer proximal to the channel layer by way of an etching process, an electron beam lithography process, a nano-imprinting process, or a thermal etching process, or a combination thereof.

17. The method of claim 13, wherein the forming the plurality of second channels extending along the second direction in the first layer where the channel layer is located, or in the second layer where the channel layer and the guide layer are located, such that each second channel of the plurality of second channels is in communication with the plurality of first channels comprises:
forming a plurality of second grooves extending in the second direction and in communication with each first channel of the plurality of first channels, on the first layer where the channel layer is located, or on the second layer where the channel layer and the guide layer are located, by using a mask corresponding to a pattern of each second channel of the plurality of second channels, by way of an etching process, and thereby forming the plurality of second channels.

18. The manufacturing method of claim 13, further comprising:
forming a planarization layer on the channel layer.

19. The manufacturing method of claim 13, wherein the guide layer is made of a glass material.

* * * * *